United States Patent
Ramsauer

(10) Patent No.: US 8,837,667 B2
(45) Date of Patent: Sep. 16, 2014

(54) BREAST POSITIONING DURING MAMMOGRAPHY EXPOSURES

(75) Inventor: Martin Ramsauer, Pyrbaum (DE)

(73) Assignee: Siemens Aktiengesellschaft, München (DE)

( * ) Notice: Subject to any disclaimer, the term of this patent is extended or adjusted under 35 U.S.C. 154(b) by 233 days.

(21) Appl. No.: 13/099,339

(22) Filed: May 2, 2011

(65) Prior Publication Data
US 2011/0268255 A1 Nov. 3, 2011

(30) Foreign Application Priority Data
May 3, 2010 (DE) .......... 10 2010 019 019

(51) Int. Cl.
*A61B 6/04* (2006.01)
(52) U.S. Cl.
USPC .......................................... 378/37; 378/208
(58) Field of Classification Search
USPC .......................................... 378/37, 204, 208
See application file for complete search history.

(56) References Cited

U.S. PATENT DOCUMENTS

| 5,040,198 A | 8/1991 | Hixson, Sr. |
| 5,189,686 A * | 2/1993 | Hixson, Sr. ................ 378/37 |
| 2004/0202279 A1 | 10/2004 | Besson et al. |
| 2008/0303457 A1 | 12/2008 | Maltz |

FOREIGN PATENT DOCUMENTS

DE 41 26 778 A1 4/1992

OTHER PUBLICATIONS

German Office Action dated Jun. 30, 2011 for corresponding German Patent Application No. DE 10 2010 019 019.5 with English translation.

* cited by examiner

*Primary Examiner* — Jurie Yun
(74) *Attorney, Agent, or Firm* — Lempia Summerfield Katz LLC

(57) ABSTRACT

The present embodiments relate to an add-on unit for an object table of a mammography device for positioning a breast of a patient during an X-ray exposure. The add-on unit permits a symmetric collimation during MLO exposures. Use of the add-on unit is less resource-intensive than mammography devices with movable compression plates. Easier placement of an inner arm of the patient on the object table is also possible.

21 Claims, 3 Drawing Sheets

BREAST POSITIONING DURING MAMMOGRAPHY EXPOSURES

This application claims the benefit of DE 10 2010 019 019.5, filed May 3, 2010.

BACKGROUND

The present embodiments relate to an add-on unit for an object table of a mammography device for positioning a patient breast during an X-ray exposure.

Female breast tissue may be screened for carcinoma development using X-ray radiation.

Owing to the particular anatomical characteristics of a region of the body that is being examined, specialized devices (e.g., mammography units) are used for the examination using X-rays.

Exposure settings of the mammography devices have evolved into standard settings for diagnostic purposes. The following two standard settings may be used:

A medio-lateral oblique (MLO) view of the breast (e.g., MLO projection) is the default setting in early breast cancer detection mammography. In this case, the breast is imaged at a 45° angle. The 45° oblique view may visualize outer upper quadrants, axillary tails and inframammary folds.

A cranio-caudal view of the breast (e.g., CC projection) may be acquired vertically from above. The CC projection may show as much breast tissue as possible and may visualize all breast segments with the exception of breast segments located furthest away laterally and axillarily.

In the course of a standard examination, 2-plane mammography may be performed. The 2-plane mammography combines the medio-lateral oblique (MLO) and the cranio-caudal (CC) views.

Mammography devices may have an object table or a lower plate, on which the breast to be imaged is placed. The breast may be compressed with the aid of a compression plate pressing onto the breast from above (e.g., the breast is clamped between the compression plate and the object table).

Good compression results in mammographic images having improved image resolution, image definition and contrast.

By reducing the breast thicknesses to be penetrated by the radiation, compression also leads to a significant dose reduction in the glandular tissue.

In the case of MLO exposures, the 45° position of the compressed breast may be unpleasant for the patient. Positioning small women (for oblique projections) on digital mammography devices having a large full field digital mammography (FFDM) of 24×30 cm, for example, causes problems. The problem of MLO positioning in the case of small women with smaller breasts is less critical with small detectors having a recording area of, for example, 18×24 cm.

In order to make the exposure easier for the patient, movable compression plates (e.g., "shift paddles") have been introduced. The mode of operation of a movable compression plate is shown in FIG. 2. A breast 10 that is to be examined is compressed using an object table 1 and a movable compression plate 2. The movable compression plate 2 is movably mounted on a retaining fixture 3 such that the movable compression plate 2 is displaceable substantially vertically with respect to the beam path. The displacement directions are indicated by the arrow 12. The retaining fixture 3 is mounted on a stand (not shown) so as to be tillable together with the object table 1. The 45° angle for the MLO exposure may be set by tilting the retaining fixture 3. This is illustrated in the figure by the ray beam 5 shown, which forms an angle of approximately 45° with the vertical. The ray beam 5 is collimated using a collimator 4.

In FIG. 2, the compressed breast 10 is positioned at an edge of the object table 1 in order to permit the arm 11 of the patient to be placed next to the object table 1. For this asymmetric positioning of the breast 10 in relation to the object table 1, the compression plate 2 is moved in the direction of a right-hand edge of the object table 1. In order to record an image of a region of the object table 1, in which the breast 10 is placed, the ray beam 5 is directed onto the region by a corresponding adjustment of the collimator 4. This may also be referred to as an asymmetric collimation, because the ray beam 5 is not directed centrally onto the object table 1.

SUMMARY AND DESCRIPTION

The present embodiments may obviate one or more of the drawbacks or limitations in the related art. For example, mammograms of a breast may be performed less resource-intensively, without additional discomfort for the patient.

An add-on unit for an object table of a mammography device for positioning a breast of a patient during an X-ray exposure is provided.

The add-on unit may be an additional part that is mounted on an object table and is configured for holding a breast (e.g., a compressed breast) of the patient during the X-ray exposure. Using the add-on unit, the breast is positioned higher compared to the table surface, thereby making more space available for an arm of the patient at a side of the object table. The object table is the part of the mammography device where conventionally the breast of the patient is positioned for a mammogram. The object table is also designated by the term "bucky cover" and may contain a detector for the X-ray exposure.

Compared with conventional solutions that use an asymmetric positioning of the breast being examined, the present embodiments are less resource-intensive. Asymmetric collimation may not be used, and an outlay for a movable compression plate is not required.

In one embodiment, the add-on unit is configured such that with a central arrangement of the add-on unit on the object table, space for an arm of the patient is available on the object table (e.g., at one or both sides) next to the add-on unit. For this purpose, the add-on unit may be smaller in diameter than the object table in a section that is raised up above the object table. In other embodiments, the diameter is smaller in the center or the entire section. The diameter relates to a direction that is parallel to the object table and essentially orthogonal to the viewing direction of the patient under examination.

The diameter may be geared to the requirements in relation to the positioning of the breast (e.g., an upper surface of the add-on unit may be marginally larger than the maximum distention of a compressed breast). The add-on unit may be configured such that the add-on unit tapers in the upper section in order to allow a better support for the underside of an arm. The tapering section may also have a concave shape in order to assist the positioning of an approximately round arm. The possibility of positioning the inner arm of the patient (e.g., the arm on the side of the breast being examined) on the object table is a further advantage compared with the approach with movable compression plate described above.

In one embodiment, the add-on unit is detachably connected to the object table. The add-on unit may be connected to the object table in a variety of ways (e.g., using plug-in connections and/or clamping connections).

In one embodiment, the add-on unit includes two sections (e.g., a first, lower section and a second section). The first, lower section is configured for partly enclosing the object table so as to enable the add-on unit to be pushed or clipped on. The second section produces an elevation with respect to the object table. The breast may be placed on the elevation (e.g., the second section stands above the object table when the add-on unit is clipped on).

In one embodiment, the add-on unit mounted on the object table is adjustable in height in order to provide an adjustment in accordance with the space used for the placement of the arm. The add-on unit may be locked at different or at any heights in terms of the height adjustment.

In another embodiment, the add-on unit is formed using CFR material (e.g., carbon-fiber-reinforced plastic).

DETAILED DESCRIPTION OF THE DRAWINGS

Figure 1:
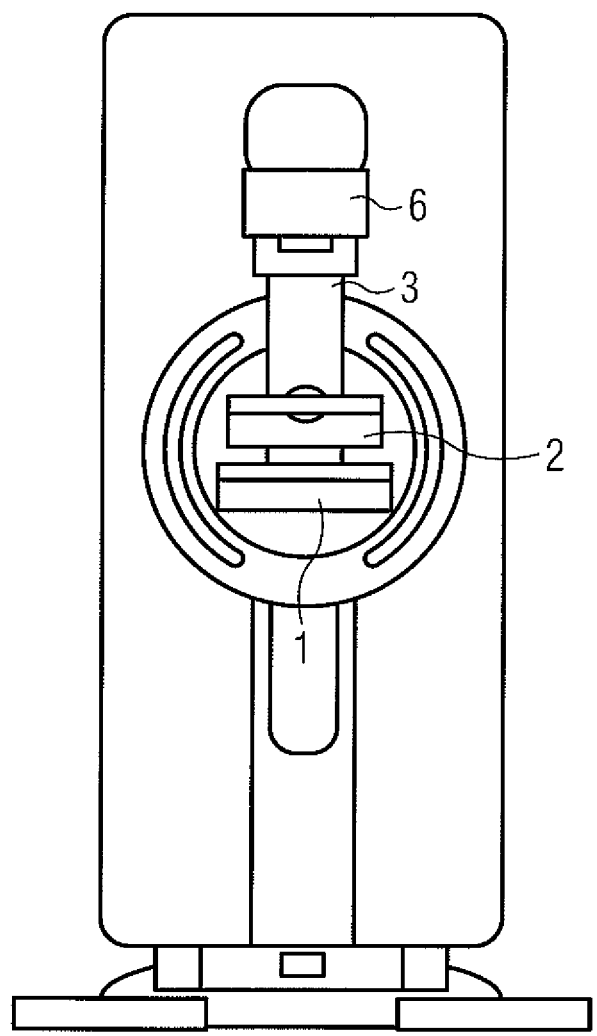
FIG. 1 shows a front view of a mammography device.
Figure 2:
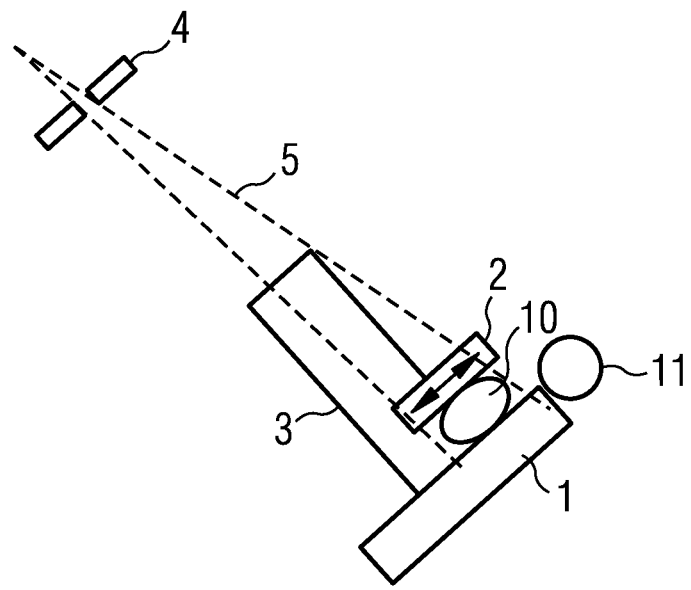
FIG. 2 is a schematic representation of a shift paddle of the prior art.
Figure 3:
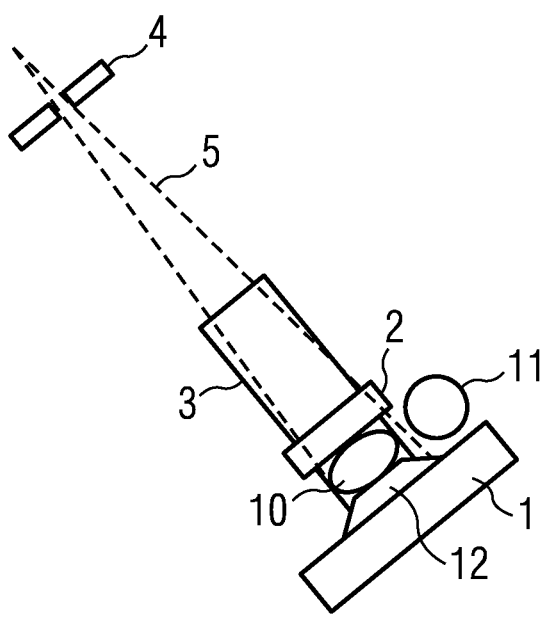
FIG. 3 shows one embodiment of a table add-on unit.

FIG. 1 shows a mammography device from the front (e.g., a patient examined therewith would be seen from the back). The mammography device includes an object table or bucky cover 1, a compression plate 2 (e.g., a shift paddle 2) and a radiation source 6 (e.g., components). The object table or bucky cover 1, the compression plate 2, and the radiation source 6 are secured to a retaining fixture 3. The bucky cover 1 contains a detector, on which an X-ray image is registered. For medio-lateral oblique (MLO) exposures, the retaining fixture 3 is rotatable about an axis together with the components. FIGS. 2 and 3 schematically show MLO exposures for a conventional solution (FIG. 2) and a solution according to the present embodiments (FIG. 3). FIG. 2 shows a procedure when positioning a breast of a patient with the aid of a shift paddle 2. The shift paddle 2 permits the breast 10 of the patient to be positioned at an edge of the object table 1 so that an arm of the patient 11 may be placed next to the object table 1. This solution is associated with extra expenditure (e.g., a movable compression plate) and results in an asymmetric collimation of the radiation onto an edge zone of the object table. The asymmetric collimation entails further overhead (e.g., to position a cassette inserted in the object table or the detector accordingly) and a more complicated determination of the angle, at which the exposure is performed (e.g., a 45° oblique exposure).

FIG. 3 shows a solution according to the present embodiments. The differences with respect to the conventional approach become clear from a comparison of FIGS. 2 and 3. A table add-on unit 12 is mounted centrally on the object table 1. This permits the breast 10 of the patient 11 to be positioned higher, thereby providing room for the an arm of the patient 11 on the object table 1 next to the table add-on unit 12 because of the greater distance between the object table 1 and the compression plate 2. It is also advantageous, compared with the solution according to FIG. 2, that the arm may be supported. The collimation of a beam 5 using a collimator 4 may be centered. The retaining fixture 3 may not be configured for a lateral displacement of the compression plate 2.

Figure 4:
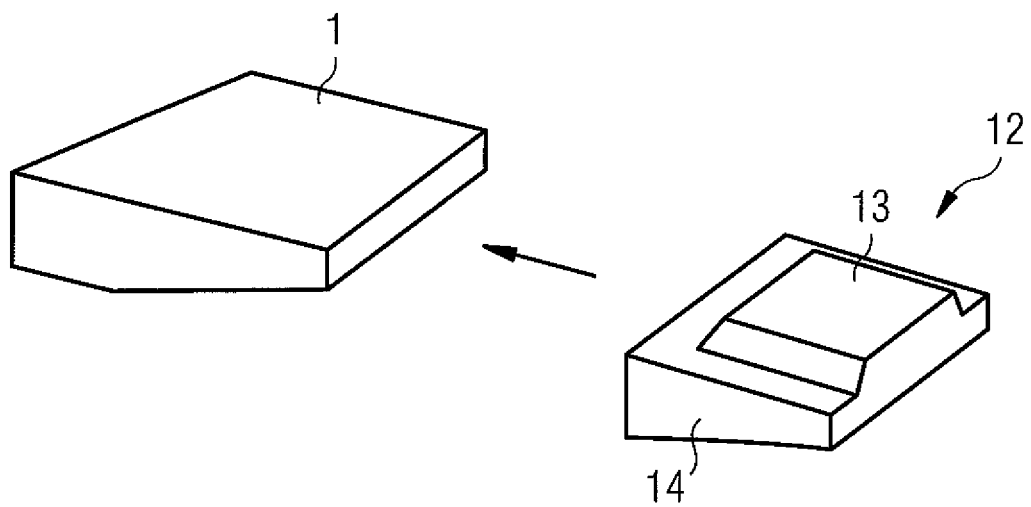
FIG. 4 shows a detailed view of one embodiment of a table add-on unit.

FIG. 4 shows additional details of the table add-on unit 12 according to the present embodiments. The table add-on unit 12 includes two sections 13 (e.g., an upper section) and 14 (e.g., a lower section). The upper section 13 is raised up above the object table 1. In one embodiment, the upper section 13 is narrower than the object table 1 and may taper or curve in an upward direction so that there is space for the arm of the patient at a side of the object table 1. The lower section 14 is configured such that the lower section 14 partly encloses the bucky cover 1 and may be pushed onto the bucky cover 1. In this arrangement, a locking device may also be provided in order to fix or secure the table add-on unit 12 in position. In one embodiment, the table add-on unit 12 is formed in one piece from CFR material (e.g., carbon-fiber-reinforced plastic).

The embodiments described above only represent some possible implementations. Other embodiments are possible. For example, the add-on unit may be configured in the form of a support that includes only the upper section 13 of the add-on unit 12 shown in FIG. 4. The support is placed onto the object table 1 and held in position by a suitable fastening device (e.g., high friction, adhesive, locking device).

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An add-on unit for an object table of a mammography device, the add-on unit for positioning a breast of a patient during an X-ray exposure, the add-on unit comprising:
    a recessed portion such that the add-on unit comprises an upper internal surface and a lower internal surface,
    wherein the add-on unit is pushable onto the object table such that the add-on unit encloses part of an upper surface of the object table and part of a lower surface of the object table, and such that the upper surface of the object table abuts the upper internal surface of the add-on unit.

2. The add-on unit as claimed in claim 1, wherein space for an arm of a patient is available on the object table next to the add-on unit when the add-on unit is centrally arranged on the object table.

3. The add-on unit as claimed in claim 2, wherein the add-on unit comprises an upper section, and
    wherein the add-on unit tapers in the upper section.

4. The add-on unit as claimed in claim 2, wherein the add-on unit is configured such that when the add-on unit is mounted on the object table, at least one section of the add-on unit is raised up above the object table and the at least one section has a smaller transverse diameter than the object table.

5. The add-on unit as claimed in claim 2, wherein the add-on unit is detachably connectable to the object table.

6. The add-on unit as claimed in claim 2, comprising:
    a first section; and
    a second section,
    wherein the first section is configured for partly enclosing the object table, and
    wherein the second section produces an elevation relative to the object table, the breast of the patient being placeable on the elevation.

7. The add-on unit as claimed in claim 1, wherein the add-on unit comprises an upper section, and wherein the add-on unit tapers in the upper section.

8. The add-on unit as claimed in claim 7, wherein the add-on unit is configured such that when the add-on unit is mounted on the object table, at least one section of the add-on unit is raised up above the object table and the at least one section has a smaller transverse diameter than the object table.

9. The add-on unit as claimed in claim 7, wherein the add-on unit is detachably connectable to the object table.

10. The add-on unit as claimed in claim 7, comprising:
a first section; and
a second section,
wherein the first section is configured for partly enclosing the object table, and
wherein the second section produces an elevation relative to the object table, the breast of the patient being placeable on the elevation.

11. The add-on unit as claimed in claim 1, wherein the add-on unit is configured such that when the add-on unit is mounted on the object table, at least one section of the add-on unit is raised up above the object table and the at least one section has a smaller transverse diameter than the object table.

12. The add-on unit as claimed in claim 11, wherein the at least one section tapers toward a top of the at least one section.

13. The add-on unit as claimed in claim 12, comprising:
a first section; and
a second section,
wherein the first section is configured for partly enclosing the object table, and
wherein the second section produces an elevation relative to the object table, the breast of the patient being placeable on the elevation.

14. The add-on unit as claimed in claim 11, wherein the add-on unit is detachably connectable to the object table.

15. The add-on unit as claimed in claim 11, comprising:
a first section; and
a second section,
wherein the first section is configured for partly enclosing the object table, and
wherein the second section produces an elevation relative to the object table, the breast of the patient being placeable on the elevation.

16. The add-on unit as claimed in claim 1, wherein the add-on unit is detachably connectable to the object table.

17. The add-on unit as claimed in claim 1, comprising:
a first section; and
a second section,
wherein the first section is configured for partly enclosing the object table, and
wherein the second section produces an elevation relative to the object table, the breast of the patient being placeable on the elevation.

18. The add-on unit as claimed in claim 1, wherein the add-on unit is mounted on the object table, and
wherein the add-on unit is adjustable in height.

19. The add-on unit as claimed in claim 1, wherein the add-on unit is formed with CFR material.

20. The add-on unit as claimed in claim 1, further comprising a locking device configured to fix a position of the add-on unit relative to the object table.

21. An object table of a mammography device, the object table comprising:
an upper surface for supporting a breast of a patient during an X-ray exposure;
a lower surface; and
an add-on device configured to position the breast of the patient during the X-ray exposure, the add-on device having a recessed portion such that the add-on device comprises an upper internal surface and a lower internal surface, the add-on device being pushable onto the upper surface such that the add-on device encloses part of the upper surface and the lower surface, and such that the upper surface is against the upper internal surface of the add-on device,
the add-on device positioning the breast such that a symmetric collimation is provided during medio-lateral oblique exposures.

\* \* \* \* \*